United States Patent [19]

Spry et al.

[11] Patent Number: 4,521,598

[45] Date of Patent: Jun. 4, 1985

[54] 3-AZIDOCEPHALOSPORINS

[75] Inventors: Douglas O. Spry, Mooresville; Wayne A. Spitzer, Indianapolis, both of Ind.

[73] Assignee: Eli Lilly and Company, Indianapolis, Ind.

[21] Appl. No.: 536,468

[22] Filed: Sep. 28, 1983

[51] Int. Cl.[3] .............. C07D 501/14; A61K 31/545
[52] U.S. Cl. .................................. 544/16; 544/22
[58] Field of Search ............ 544/16, 22, 26, 27, 544/28; 424/246

[56] References Cited

U.S. PATENT DOCUMENTS

| | | | |
|---|---|---|---|
| 3,274,186 | 9/1966 | Barker et al. | 260/243 |
| 3,278,531 | 10/1966 | Cox et al. | 260/243 |
| 3,360,515 | 12/1967 | Takano et al. | 260/243 |
| 3,634,418 | 1/1972 | Willner | 260/243 C |
| 3,923,795 | 12/1975 | Spry | 260/243 |
| 4,001,226 | 1/1977 | Spry | 260/243 C |
| 4,420,478 | 12/1983 | Heymes | 424/246 |

*Primary Examiner*—Nicholas S. Rizzo
*Attorney, Agent, or Firm*—William B. Scanlon; Arthur R. Whale

[57] ABSTRACT

7β-Acylamino-3-azido-3-cephem-4-carboxylic acid esters are obtained with the corresponding 3-halo or 3-sulfonyloxy-3-cephem esters and an alkali metal azide. The 3-azido compounds as the free acids or salts are antibacterial agents while in esterified form react with alcohols and phenols to provide 2-alkoxy (or 2-phenoxy)-3amino-3-cephem esters and isomeric ring expanded 4,7-bicyclo β-lactam compounds, namely [2R-(2α,-7α,8β)-4-alkoxy (or 4-phenoxy)-9-oxo-8-acylamino-6-thia-1,3-diazabicyclo[5.2.0]non-3-ene-2-carboxylic acids and esters and the corresponding 3-alkoxy (or 3-phenoxy) 1,4-diazabicyclo[5.2.0]non-3-ene-2-carboxylic acids and esters. These reaction products obtained with the azide possess antibacterial properties.

12 Claims, No Drawings

3-AZIDOCEPHALOSPORINS

BACKGROUND OF THE INVENTION

A number of cephalosporin antibiotics having a substituent directly substituted on the carbon at the 3-position of the cephem ring system are known. For example, the 3-hydroxy and 3-methoxy substituted 3-cephem compounds described by Chauvette in U.S. Pat. Nos. 3,917,587 and 3,917,588; the 3-halo-3-cephem compounds described by Chauvette in U.S. Pat. Nos. 3,925,372 and 3,962,227; the 3-sulfonyloxy-3-cephem and 3-sec.-amino-3-cephem compounds described by Spitzer in U.S. Pat. Nos. 3,985,737 and 4,013,651, respectively; and the 3-heterocyclic thio substituted 3-cephems described in U.S. Pat. No. 3,992,377. Many 3-substituted methyl-3-cephem compounds are known in the cephalosporin art. Among the 3-substituted methyl-3-cephem compounds which have been described are the 3-azidomethyl substituted cephalosporins, U.S. Pat. Nos. 3,274,186, 3,278,531, 3,360,515 and 3,634,418. The 3-azidomethyl-3-cephem compounds have been converted to 3-aminomethyl-3-cephem antibiotics and Heymes et al. have prepared cephalosporin γ-lactams with the 3-aminomethyl-3-cephem compounds. 7-Azido cephalosporins are disclosed as useful intermediates by Christensen et al. in U.S. Pat. No. 4,297,488.

SUMMARY OF THE INVENTION

This invention relates to 3-azido cephalosporin antibacterial compounds. In particular, it relates to 7-amino and 7-acylamino-3-azido-3-cephem-4-carboxylic acids and to the esters and salts thereof. The 3-azido-3-cephems are prepared by reacting an ester of a 3-halo-3-cephem or 3-alkylsulfonyloxy-3-cephem with an alkali metal azide in dimethylformamide or other solvent. The 3-azido ester is deesterified to provide the 3-azido-3-cephem-4-carboxylic acid. The latter can be converted to a salt form, eg. the sodium or potassium salt, by conventional means. The 3-azido-3-cephems as the free carboxy compounds or in a salt form thereof inhibit the growth of microorganisms pathogenic to man and animals. The compounds of the invention also are useful intermediates which can be converted to 6-thia-1,3-diazabicyclo[5.2.0]nonenes, 6-thia-1,4-diazabicyclo[5.2.0]nonenes, and 3-amino-2-substituted-3-cephem compounds having antibacterial activity.

DETAILED DESCRIPTION

The 3-azido-3-cephem compounds provided by this invention are represented by the following structural formula 1

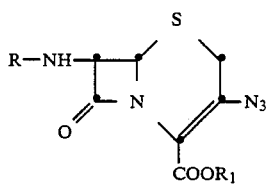

wherein
R is hydrogen or an acyl group of the formula

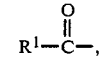

wherein
$R^1$ is $C_1$–$C_4$ alkyl, $C_1$–$C_4$ alkyl substituted by halogen or cyano;
or R is an aroyl or aralkanoyl group of the formula

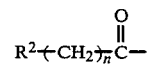

wherein
$R^2$ is phenyl or a mono substituted phenyl group of the formula

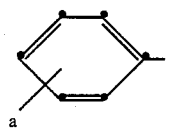

wherein
a is halogen, amino, hydroxy, $C_1$–$C_4$ alkyl, $C_1$–$C_4$ alkoxy, cyano, hydroxymethyl, aminomethyl, carboxamido, carboxymethyl, or $C_1$–$C_4$ alkoxycarbonylmethyl;
or $R^2$ is a di- or tri-substituted phenyl group of the formula

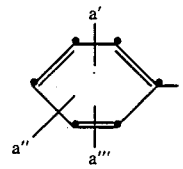

wherein
a′, a″, and a‴ are independently hydrogen, halogen, hydroxy, $C_1$–$C_4$ alkyl, or $C_1$–$C_4$ alkoxy; and
n is 0 or 1;
or R is a heteroarylalkanoyl group of the formula

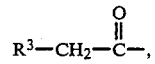

wherein
$R^3$ is

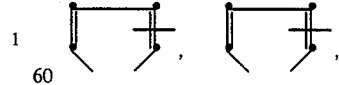

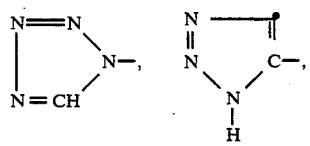

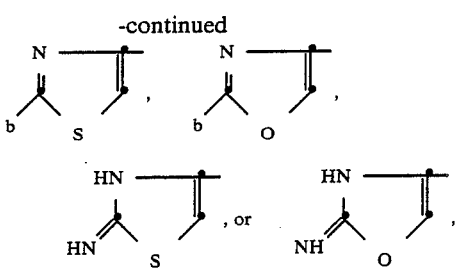

wherein
each b is amino, protected amino, $C_1$-$C_3$ alkyl or phenyl;
or R is an aryloxyacetyl or arylthioacetyl group of the formula

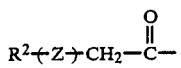

wherein
$R^2$ has the same meanings as defined above and Z is O or S;
or R is an α-substituted aralkanoyl or heteroarylalkanoyl substituted group of the formula

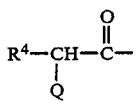

wherein
$R^4$ is $R^2$, as defined above, and in addition is thienyl, furyl, or 1,4-cyclohexadienyl; Q is hydroxy, formyloxy, carboxy, the sulfo group —$SO_3H$, or amino;
or R is an oximino-substituted aralkanoyl or heteroarylalkanoyl group of the formula

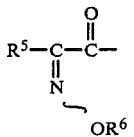

wherein
$R^5$ is $R^2$ and $R^3$ as each is defined above, and $R^6$ is hydrogen or $C_1$-$C_3$ alkyl;
$R_1$ is hydrogen or a carboxy protecting group; and when $R_1$ is hydrogen the pharmaceutically acceptable non-toxic salts thereof.

The term $C_1$-$C_4$ alkyl as used herein refers to methyl, ethyl, n-propyl, iso-propyl, n-butyl, sec-butyl, and t-butyl; $C_1$-$C_4$ alkoxy refers to methoxy, ethoxy, n-propoxy, n-butoxy, t-butoxy, and like $C_1$-$C_4$ alkoxy groups; and halogen refers to fluoro, chloro, bromo, or iodo.

Examples of acyl groups represented by R in the formula 1 when R is R'—C(O)— are acetyl, propionyl, butyryl, chloroacetyl, and cyanoacetyl; when R is an aroyl or aralkanoyl group examples include benzoyl, 4-chlorobenzoyl, 2,6-dimethoxybenzoyl, 4-hydroxybenzoyl, 4-methylbenzoyl, 4-methoxybenzoyl, 3,4-dichlorobenzoyl, 3-cyanobenzoyl, 4-methoxycarbonylmethylbenzoyl, 4-ethylbenzoyl, 4-bromo-3-methylbenzoyl, 4-t-butylbenzoyl, 2-fluorobenzoyl, 3-hydroxybenzoyl, 4-carbamoylbenzoyl, 2-aminomethylbenzoyl, 3-ethoxybenzoyl, phenylacetyl, 4-chlorophenylacetyl, 4-methylphenylacetyl, 4-hydroxyphenylacetyl, 3,4-dimethylphenylacetyl, 2-aminomethylphenylacetyl, 4-methoxyphenylacetyl, 2,6-dimethoxyphenylacetyl, 4-ethoxyphenylacetyl, 3-bromophenylacetyl, 3,4-dihydroxyphenylacetyl, 3,5-dichloro-4-hydroxyphenylacetyl, 3-chloro-4-hydroxyphenylacetyl, 3-ethoxy-4-hydroxyphenylacetyl, 4-cyanophenylacetyl, 4-carboxyphenylacetyl, 4-carboxymethylphenylacetyl, 4-t-butylphenylacetyl, 3,4,5-trihydroxyphenylacetyl, and 3-bromo-4-ethoxyphenylacetyl; and when R is a heteroarylalkanoyl group examples of R include 2-thienylacetyl, 3-thienylacetyl, 2-furylacetyl, 1H-tetrazol-1-ylacetyl, 2H-tetrazol-5-ylacetyl, thiazol-4-ylacetyl, oxazol-4-ylacetyl, 2-methylthiazol-4-ylacetyl, 2-aminothiazol-4-ylacetyl, and 2-phenyloxazol-4-ylacetyl; and when R is an aryloxyacetyl or arylthioacetyl group examples include phenoxyacetyl, 4-chlorophenoxyacetyl, 3,4-dichlorophenoxyacetyl, 4-methylphenylacetyl, 4-fluorophenoxyacetyl, 4-hydroxyphenoxyacetyl, 3-chloro-4-methoxyphenoxyacetyl, 4-ethoxyphenoxyacetyl, phenylthioacetyl, 4-chlorophenylthioacetyl, 3,5-dichlorophenylthioacetyl, 4-fluorophenylthioacetyl, 3,4-dichlorophenylthioacetyl, 4-bromophenylthioacetyl, and 4-chloro-3-methylphenylthioacetyl; and when R is an α-substituted aralkanoyl or heteroarylalkanoyl group examples include phenylglycyl, 4-hydroxyphenylglycyl, 4-ethoxyphenylglycyl, 4-chlorophenylglycyl, 3-chloro-4-hydroxyphenylglycyl, 2-thienylglycyl, mandeloyl, malonyl, α-sulfophenylacetyl, and α-amino-1,4-cyclohexadien-1-ylacetyl; and when R is an oximino-substituted acyl group examples of such groups are α-hydroxyiminophenylacetyl, α-methoximinophenylacetyl, α-methoximino-2-furylacetyl, α-methoximino-2-thienylacetyl, α-hydroxyimino-(2-aminothiazol-4-yl)-acetyl, and α-methoximino-(2-aminothiazol-4-yl)acetyl.

The term "protected amino" as used herein refers to the amino group substituted by a conventional amino protecting group commonly used in the cephalosporin and peptide arts. Examples of such groups are the alkyloxycarbonyl and aralkyloxycarbonyl groups such as methoxycarbonyl, ethoxycarbonyl, t-butoxycarbonyl BOC, trichloroethoxycarbonyl, benzyloxycarbonyl, p-nitrobenzyloxycarbonyl, and diphenylmethoxycarbonyl; the alkenyloxycarbonyl and alkinyloxycarbonyl groups, eg. allyloxycarbonyl and the dialkylethinylcarbinyloxycarbonyl groups, such as dimethylethinylcarbinyloxycarbonyl; the cycloalkoxycarbonyl groups, eg. cyclopentyloxycarbonyl and cyclohexyloxycarbonyl; the β-ketoesters which form enamines with the amino group, eg. ethyl acetoacetate and methyl acetoacetate; the aryl protecting groups such as trityl, the silyl protecting groups such as trialkylsilyl such as trimethylsilyl and dimethylbutylsilyl; acyl and diacyl groups such as acetyl, chloroacetyl, and phthaloyl; and other commonly used amino protecting groups.

The term "carboxy protecting group" refers herein to the ester forming groups which are readily removable under mild hydrolysis or hydrogenolysis conditions and which are commonly employed in the β-lactam and polypeptide arts for the temporary protection of the carboxy group. Examples of such groups are the alkyl and substituted alkyl group, eg. t-butyl, 2,2,2-trichloroethyl, 2,2,2-tribromoethyl, and 2-iodoethyl; the aralkyl groups such as benzyl, 4-nitrobenzyl, 4-methoxybenzyl, and diphenylmethyl; the trialkylsilyl groups such as trimethylsilyl, triethylsilyl, and dimethyl-t-butylsilyl; phenacyl and substituted phenacyl groups; the N-oxysuccinimido and N-oxyphthalimido groups; and like ester forming groups.

Among the 7β-acylamino 3-azido cephalosporins represented by the formula 1, certain are preferable to others. For example, the compounds wherein R is

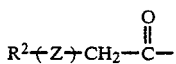

such as the phenoxyacetyl substituted compounds are preferred. Likewise, the heteroarylalkanoyl substituted compounds wherein R is

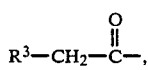

eg. 2- or 3-thienylacetyl are preferred. Further preferred 3-azido compounds are represented when R is the

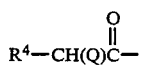

acyl group especially wherein Q is hydroxy, carboxy, or amino; and the

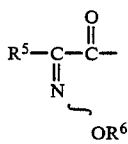

substituted 3-azido compounds wherein $R^5$ is especially phenyl, thienyl, furyl, or 2-amino-1,3-thiazol-4-yl and $R^6$ is methyl.

The 3-azido compounds represented by the formula 1 when R is hydrogen are represented by the following formula 2

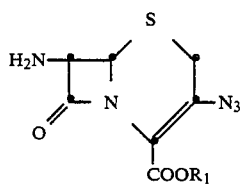

wherein $R_1$ has the same meanings as defined hereinabove for formula 1, and the salts thereof formed with inorganic acids and organosulfonic acids. Salts formed with inorganic acids are, for example, the hydrochloride, hydrobromide, sulfate, and phosphate salts. Salts formed with organosulfonic acids are, for example, the $C_1$–$C_4$ alkylsulfonates such as the methanesulfonate salt and the n-butanesulfonate salt, and the arylsulfonate salts such as the benzenesulfonate salt and the p-toluenesulfonate salt.

The compounds of the invention (formula 1) wherein R is an acyl group are prepared with a 3-halo-3-cephem ester or a 3-alkylsulfonyloxy-3-cephem ester represented by the formula 3

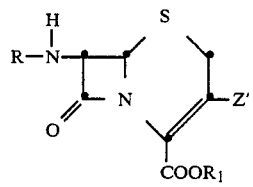

wherein Z' is halogen or $C_1$–$C_4$ alkyl $SO_2$—O—; $R_1$ is a carboxy protecting group, and R is other than hydrogen as defined for formula 1.

In formula 3, halogen is preferably chloro or bromo. The 3-halo or 3-alkylsulfonyloxy-3-cephem is reacted with an alkali metal azide, preferably sodium azide in an inert solvent. The azides (formula 1) also can be prepared with the 3-halo-3-cephem esters and tetramethylquanidinium azide (TMGA). The reaction is carried out in an inert solvent in which the starting material and the azide are at least partially soluble. Suitable solvents for the reaction with an inorganic azide are dimethylformamide, dimethylacetamide and dimethylsulfoxide. With TMGA as the azide other organic solvents such as tetrahydrofuran, acetonitrile, and methylene chloride also may be used. The reaction may also be carried out in an aqueous organic two phase heterogeneous solvent system by using a phase transfer agent such as a tetraalkylammonium salt.

The reaction is carried out at a temperature between about 0° C. and about 45° C. and preferably at about 5° C. to about 25° C.

Alternatively, the cephalosporin azides of the invention can be prepared by the N-acylation of a 7-amino-3-azido-3-cephem-4-carboxylic acid ester represented by formula 2. The N-acylation is carried out by employing the acylation methods commonly used in the N-acylation of the cephalosporin 7-amino nucleus compounds such as 7ACA, 7ADCA, and 7-amino-3-halo-3-cephem esters. For example, the acylation can be carried out under non-aqueous conditions in an organic solvent such as methylene chloride, acetonitrile, or tetrahydrofuran, or mixtures thereof, by coupling an active derivative of the carboxy group of the desired carboxylic acid with the 7-amino-3-azido-3-cephem ester (2). Active derivatives suitable for acylation purposes are acid halides, acid azides, mixed anhydrides and active esters. When an acid halide such as the chloride is used in the acylation, an acid binding agent is also used. Tertiary amines such as triethylamine, or amines such as pyridine and quinoline are suitable acid binding agents.

Active esters which can be used are those formed with the acid and an N-hydroxyheterocyclic in the presence of a condensing agent, N-hydroxysuccinimide, N-hydroxyphthalimide, and hydroxybenzotriazole (HBT) are useful active ester forming compounds. Condensing agents such as the carbodiimides eg., dicyclohexylcarbodiimide and diethylcarbodiimide can be used to form the active ester.

It is also possible to acylate the 7-amino-3-azido nucleus ester (2) by condensing the acid and the 7-amino compound with a carbodiimide such as dicyclohexylcarbodiimide.

The acid may also be converted to the mixed anhydride ester of the acid formed by the reaction of the acid with an ester of chloroformic acid. Suitable are ethyl chloroformate and iso-butyl chloroformate. The anhydride ester is formed in the presence of a hydrogen halide acceptor such as triethylamine (TEA). The preparation of the active derivative is illustrated below where in the acid

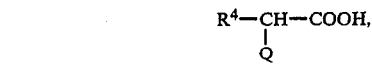

R₄ and Q are defined hereinabove.

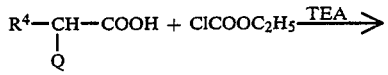

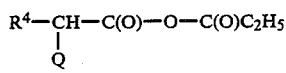

During the acylation of a 7-amino-3-azido ester, any free amino and carboxy groups also present in the carboxylic acid acylating moiety are desirably protected. For example, in formula 1 when Q is amino or carboxy, these groups are suitably protected during the acylation, and thereafter may be deprotected to provide the antibacterial form of the 3-azido compound.

The compounds of the invention, formula 1, wherein R is hydrogen are prepared with a 3-halo (or alkylsulfonyloxy)-7-amino-3-cephem ester and an azide by following the procedures described above for the preparation of 7-acylamino-3-azido cephalosporin esters. Alternatively, the 7-amino group of the 3-halo or 3-sulfonyloxy nucleus ester can be protected with an amino-protecting group prior to reaction with the azide, and thereafter the protecting group is removed. Particular protecting groups useful for this purpose are the alkoxycarbonyl, substituted alkoxycarbonyl, cycloalkoxycarbonyl, aryloxycarbonyl groups; and adamantyloxycarbonyl; the diacyl groups formed with dicarboxy compounds, the trityl group, and the "Ox" protecting group formed with the 7-amino compound and 1,2-diphenyl-1,2-ethenediolcyclic carbonate. These protected 7-amino-3-azido-3-cephem esters are represented by the following structural formula 4

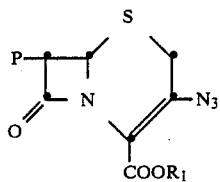

4

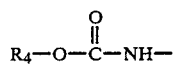

wherein P is a monoacylamino group $$R_4-O-\overset{O}{\underset{\|}{C}}-NH-$$

wherein R₄ is $C_1-C_5$ alkyl, halo-substituted $C_1-C_5$ alkyl, $C_3-C_7$ cycloalkyl, benzyl, nitrobenzyl, halobenzyl, methoxybenzyl, diphenylmethyl, or adamantyloxycarbonyl; or P is a diacylamino group represented by the formula

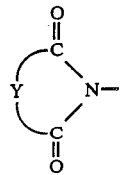

wherein Y is $C_1-C_3$ alkylene or phenylene, or the 4,5-diphenyl-4-oxazolin-2-one (Ox) represented by the formula

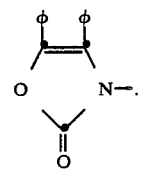

Examples of amino-protecting groups

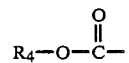

of the above formula are methoxycarbonyl, ethoxycarbonyl, t-butoxycarbonyl, n-amyloxycarbonyl, trichloroethoxycarbonyl, cyclopropoxycarbonyl, cyclopentoxycarbonyl, cyclohexoxycarbonyl, benzyloxycarbonyl, 4-nitrobenzyloxycarbonyl, diphenylmethoxycarbonyl, and adamantyloxycarbonyl. Examples of amino-protected groups P are phthalimido, succinamido, and glutarimido.

Examples of amino-protected 3-azido esters represented by the formula 4 are p-nitrobenzyl 7-(t-butyloxycarbonylamino)-3-azido-3-cephem-4-carbonylate, p-methoxybenzyl 7-(2,2,2-trichloroethoxycarbonylamino)-3-azido-3-cephem-4-carboxylate, diphenylmethyl 7-(t-butyloxycarbonylamino)-3-azido-3-cephem-4-carboxylate, p-nitrobenzyl 7-phthalimido-3-azido-3-cephem-4-carboxylate, p-nitrobenzyl 7-(4,5-diphenyl-4-oxazolin-2-one-1-yl)-3-azido-3-cephem-4-carboxylate and 2,2,2-trichloroethyl 7-(4,5-diphenyl-4-oxazolin-2-one-1-yl)-3-azido-3-cephem-4-carboxylate.

The 7-amino-3-azido nucleus compounds (formula 1, R=H) also can be prepared if desired by the N-deacylation of a 7-acylamino-3-azido-3-cephem-4-carboxylic acid ester (formula 1, R is other than H, R₁ is a protecting group). The N-deacylation is carried out by reacting the 7-acyl ester with an imido halide forming reagent to form the imido halide of the 7-amido group. An alcohol or alkyl diol compound is added to the imido halide to form the corresponding imino ether and the latter is degraded to the 7-amino compound. Useful imido halide forming reagents are, eg. phosphorous pentachloride or phosphorus trichloride, while the lower alcohols such as methyl alcohol, ethyl alcohol or isobutyl alcohol serve as suitable imino ether forming reagents. The N-deacylation is carried out in a halogenated hydrocarbon solvent such as methylene chloride or trichloroethane.

In general, the imido halide forming step is carried out at a temperature between about −5° C. and about 45° C. while the formation of the imino ether is done at lower temperatures between about −35° C. to about 5° C. Following imino ether formation the reaction mixture is warmed to about 20° C.-25° C. and, upon addition of water or via spontaneous degradation, the imino ether is hydrolyzed or decomposes to form the 7-amino-3-azido ester.

The 7-acylamino-3-azido-3-cephem-4-carboxylic acids and the salts thereof inhibit the growth of bacteria pathogenic to man and animals. The antibacterial activity is demonstrated in standard in vitro tests wherein the 3-azido free acids or salts thereof are tested against representative bacteria. For example, 7β-(2-thienylacetamido)-3-azido-3-cephem-4-carboxylic acid inhibited the growth of various organisms as shown in the following Table 1.

TABLE 1

In vitro Antibacterial Activity of 7β-(2-Thienylacetamido)-3-azido-3-cephem-4-carboxylic Acid - Disc Plate Assay

| Test Organism | Zone of Inhibition (mm)[1] |
|---|---|
| Staphylococcus aureus | 30 |
| Bacillus subtilis | 30 |
| Bacillus stearothyermophilus | 20 |
| Micrococcus luteus | 23 |
| Proteus vulgaris | 25 |
| Salmonella gallinarum | 19 |
| Escherichia coli | 21 |
| Pseudomonas solanacearum | 29 |

[1] concentration 1 mg./ml.

In the same test at the same concentration the test compound failed to produce a detectable zone of inhibition against the yeast and fungi *Saccharomyces postorianus*, *Candida albicans*, and *Trichophyton mentagrophytes*, and the bacteria *Pseudomonas aeruginosa* and *Serratia marcescens*.

In a standard agar dilution test the same test compound of the invention also inhibited the growth of a number of pathogenic bacteria as shown in Table 2 below.

TABLE 2

In vitro Antibacterial Activity of 7β-(2-Thienylacetamido)-3-azido-3-cephem-4-carboxylic Acid-Agar Dilution Method

| Test Organism | MIC (mcg./ml.) |
|---|---|
| Staphylococcus aureus X1.1 | 8 |
| Staphylococcus aureus V41 | 64 |
| Staphylococcus aureus X400 | 128 |
| Staphylococcus aureus S13E | 64 |
| Streptococcus epidermidis EP11 | 16 |
| Streptococcus epidermidis 222 | 4 |
| Streptococcus pyogenes C203 | .5 |
| Streptococcus pneumoniae Park | .25 |
| Streptococcus sp. D X66 | 128 |
| Streptococcus sp. D 2041 | 128 |
| Haemophilus influenzae C.L. | 16 |
| Haemophilus influenzae 76 | 4 |
| Escherichia coli N10 | 64 |
| Escherichia coli EC14 | 16 |
| Escherichia coli TEM | 128 |
| Klebsiella pneumoniae X26 | 4 |
| Klebsiella pneumoniae KAE | 128 |
| Klebsiella pneumoniae X68 | 16 |
| Enterobacter aerogenes C32 | 128 |
| Enterobacter aerogenes EB17 | 128 |
| Enterobacter cloacae EB5 | 128 |
| Enterobacter cloacae 265A | 128 |
| Salmonella typhi X514 | 16 |
| Salmonella typhi 1335 | 16 |

In the above test the test compound had an mic. of 128 or greater against strains of Pseudomonas, Serratia, and Proteus.

The compounds of the invention (formula 1) wherein $R_1$ is a carboxy protecting group are deesterified to the free acid form ($R_1$=H) by following known procedures. A preferred carboxy protecting ester group useful in the preparation of the 3-azido cephalosporins of the invention is the p-nitrobenzyl ester group. The 3-azido p-nitrobenzyl esters are readily deesterified to provide the 3-azido free carboxylic acids by treatment with zinc and hydrochloric acid at a temperature of about 5° C. to about 10° C.

The 3-azido cephalosporin esters represented by the formula 1 ($R_1$=protecting group) are also useful as intermediates for 2-substituted-3-amino cephalosporins represented by the following formula 5 and the fused 4:7 bicyclic β-lactam compounds represented by formula 6.

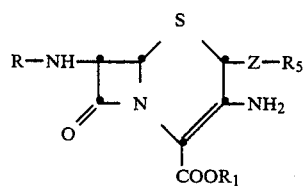

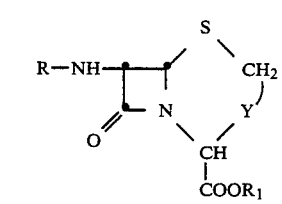

In the above formulae R and $R_1$ have the same meanings as defined for formula 1; $R_5$ is $C_1$–$C_4$ alkyl, phenyl, or substituted phenyl; Z is O or S; and Y is a divalent radical (a) or (b)

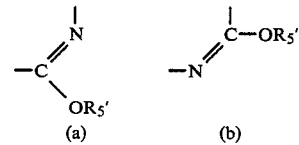

wherein $R_5'$ is $C_1$–$C_3$ alkyl, phenyl, or substituted phenyl.

The 3-azido-3-cephem esters react with lower alkanols, phenol, substituted phenols, thiophenol, substituted thiophenols, and lower alkyl thiols to provide the intermediates of the above formula 5 and while the lower alkanols and phenols react to provide compounds of formula 6. The 2-substituted-3-amino-3-cephem esters represented by formula 5 wherein Z is S are obtained by reacting the 3-azido ester with a thiophenol or alkyl thiol. The reaction, in addition to forming a 2-thio-substituted-3-cephem, also proceeds by reduction of the 3-azido group to the amine. The reaction product (formula 5) is accompanied by the 3-amino-3-cephem ester which apparently results from reduction of the 3-azido group without concomitant 2-position substitution. The reaction of the 3-azido ester with the thiol is carried out in an inert solvent at a temperature between about 45° C. and about 75° C. Excess thiol is used and in general about 3–5 equivalents is sufficient for best results. Laboratory size reactions are usually complete in about 90 minutes. Halogenated hydrocarbons such as dichloroethane, methylene chloride and the like are suitable solvents in the reaction.

The 2-thio-substituted-3-amino-3-cephem ester is isolated and separated from the co-produced 3-amino ester via chromatography over silica gel.

The compounds represented by the formula 5 wherein Z is O and the ring expanded compounds represented by the formula 6 are prepared by the reaction of a 3-azido-3-cephem ester with a lower alkanol, phenol or a substituted phenol. The reaction of the 3-azido ester with the alkanol or phenol provides in most cases a mixture of the three isomeric products as illustrated in the reaction scheme below wherein ethyl alcohol is the lower alkanol.

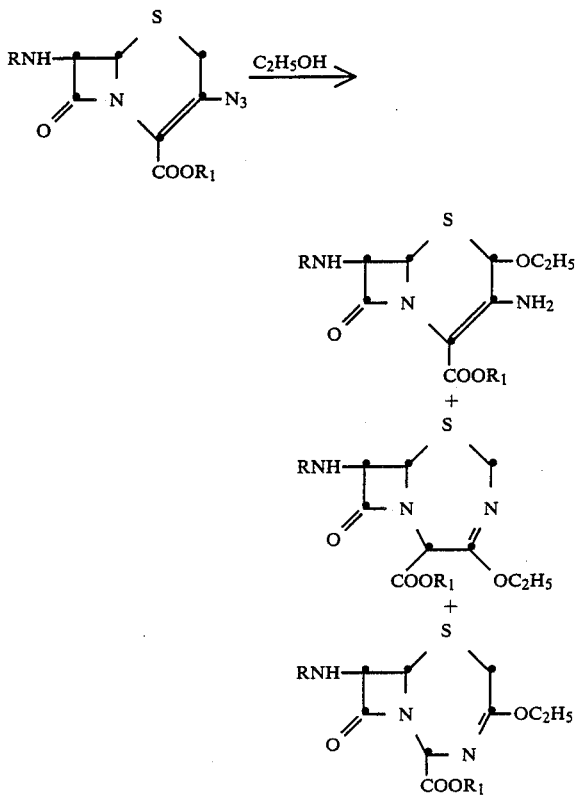

wherein $R_1$ is an ester group.

The reaction is carried out in an inert solvent such as acetone, methylethyl ketone, tetrahydrofuran or methylene chloride at a temperature between about 45° C. and about 75° C. with an excess of the alkanol or phenol. The reaction proceeds rapidly and usually is complete in about an hour with laboratory scale reactions. Preferably, the reaction is carried out in acetone at the reflux temperature with at least three molar equivalents excess of the alkanol or phenol. The products are isolated and separated from each other by chromatography over silica gel. The compounds represented by the formula 6 wherein Y is radical (b) are obtained as the predominant product in the reaction.

In the above formulae 5 and 6 the term $C_1-C_4$ alkyl refers to the straight and branched chain lower alkyl groups such as, for example, methyl, ethyl, n-propyl, n-butyl, and t-butyl; substituted phenyl refers to halophenyl, eg. 4-chlorophenyl, 3-chlorophenyl, 3-bromophenyl, 4-fluorophenyl, 2-fluorophenyl, and the like; $C_1-C_4$ alkoxyphenyl, eg. 4-methoxyphenyl, 3-ethoxyphenyl, 3,4-dimethoxyphenyl, 4-t-butoxyphenyl, and the like; alkylphenyl, eg. 4-methylphenyl, 4-t-butylphenyl, 3-methylphenyl, 3,4-dimethylphenyl, 4-isopropylphenyl, and the like.

The compounds represented by formulae 5 and 6 are isomeric with one another. Those of formula 5 are 2,3-disubstituted cephem compounds while those of formula 6 possess a 7-membered thiadiazepine ring fused to the 4-membered β-lactam ring. The formula 6 compounds are numbered herein according to the ACS system as follows.

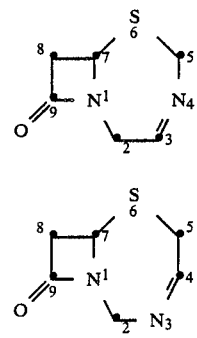

The compounds of the formula 6 are named either as 6-thia-1,3-diazabicyclo[5.2.0]non-3-enes (formula 6 Y=b) or 6-thia-1,4-diazabicyclo[5.2.0]non-3-enes.

The 7-membered thiadiazepine compounds represented by formula 6 lack the chromophore chracteristics of the cephalosporin 3-cephem compounds such as those represented by formula 5. The formula 5 compounds are distinguishable from the formula 6 compounds in that the latter do not show the characteristic 3-cephem absorption in the UV.

As with the 3-azido cephalosporins of this invention, the compounds represented by formulae 5 and 6 wherein R is hydrogen may, if desired, be prepared by the N-deacylation of an N-acyl compound (R is other than H, formulae 5 and 6). The N-deacylation is carried out by the same procedures as described above for the N-deacylation of a 3-azido compound. The 7-amino-2-substituted-3-amino nucleus compound and the 8-amino bicyclo nonene nucleus compound obtained via the N-deacylation are represented by the following formulae 5' and 6'

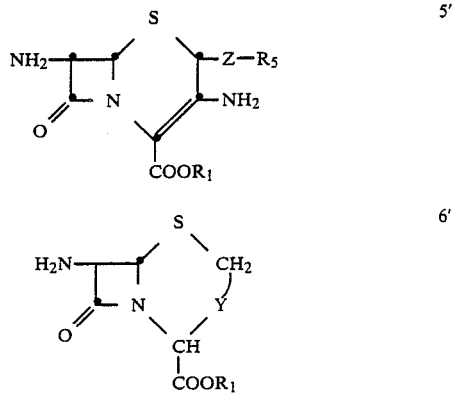

wherein $R_1$, $R_5$, and Y have the same meanings as defined hereinabove for formulae 5 and 6.

The above nucleus compounds can be acylated on the amino group by following the acylating procedures described hereinabove for the acylation of the 7-amino-3-azido-3-cephem nucleus ester.

The 3,7-diamino-3-cephem compounds (formula 5') and the 8-amino-bicyclononenes (formula 6') form acid addition salts with the mineral acids and the organic sulfonic acids. For example, such salts include the hydrochloride, hydrobromide, sulfate, and phosphate mineral acid salts and the methanesulfonate, p-toluene-sulfonate, and naphthalenesulfonate sulfonic acid salts. These salts are useful stable forms of the nuclei for use in isolation, purification and storage of the nuclei.

The compounds represented by formula 6 are preferred compounds of this invention and especially the 1,3-diazabicyclonon-3-enes represented when Y is $-N=C(OR_5')-$(b) and $R_5'$ is methyl or ethyl. Further preferred compounds of this type are represented by formula 6 wherein R is the acyl groups

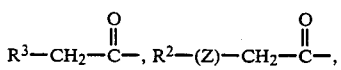

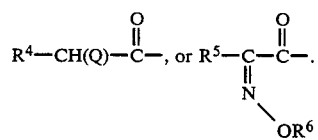

Examples of such preferred bicyclo nonenes are represented when R is phenylacetyl, phenoxyacetyl, 2-thienylacetyl, phenylthioacetyl, mandeloyl, malonyl, D-phenylglycyl, D-p-hydroxyphenylglycyl, α-methoxyiminophenylacetyl, α-methoxyimino-2-amino-1,3-thiazole-4-ylacetyl, α-methoxyimino-2-furylacetyl, and $R_5'$ is methyl or ethyl.

The 3-amino-2-substituted-3-cephem compounds (formula 5) as the free acids or salts thereof and the bicyclo nonenes (formula 6) as the free acids or salts thereof are antibacterial agents which inhibit the growth of bacteria pathogenic to man and animals. In Table 3 below the in vitro antibacterial properties of the three isomeric products represented by formulae 5 and 6 obtained in the disc-plate method is tabulated.

TABLE 3

| In Vitro Antibacterial Activity-Disc Plate | | | |
|---|---|---|---|
| | Test Compound[1] Zone of Inhibition (mm. diam.) Concentration: 3 mg./ml. | | |
| Test Organism | A | B | C |
| Staphylococcus aureus | 18 | 29 | 29 |
| Bacilus subtilis | 15 | 27 | 30 |
| Micrococcus luteus | 10 | 25 | 24 |
| Trichophyton mentagrophytes | tr.[2] | — | — |
| Candida albicans | — | 13 | — |
| Bacillus stearothyermophilus | 11 | 34 | 36 |
| Escherichia coli | 12 | 25 | 30 |
| Pseudomonas solanacearum | — | 12 | 11 |
| Proteus vulgaris | — | — | tr. |

[1]Compound A: [2R—(2α,7α,8β)-4-methoxy-9-oxo-8-[(2-thienylacetyl)amino]-6-thia-1,3-diazabicyclo[5.2.0]non-3-ene-2-carboxylic acid, sodium salt.
Compound B: [2R—(2α,7α,8β)-3-methoxy-9-oxo-8-[(2-thienylacetyl)amino]-6-thia-1,4-diazabicyclo[5.2.0]non-3-ene-2-carboxylic acid, sodium salt.
Compound C: sodium 7β-[(2-thienylacetyl)amino]-2-methoxy-3-amino-3-cephem-4-carboxylate.
[2]tr. indicates a trace zone of inhibition.

The 7β-acylamino-3-azido-3-cephem-4-carboxylic acids (formula 1, R=acyl), the 7β-acylamino-2-substituted-3-amino-3-cephem-4-carboxylic acids (formula 5, R=acyl), and the isomeric 8β-acylaminobicyclodiazanonene-2-carboxylic acids (formula 6, R=acyl) and the pharmaceutically acceptable salts thereof may be used for topical application to sores, cuts, and abrasions to treat or prevent bacterial infection. They also may be administered parenterally or orally in the treatment of bacterial infections. For such uses the compounds as free acids or as salts thereof can be formulated into capsules, tablets, or liquid suspensions for oral administration. For injectable use the compounds can be formulated as suspensions or solutions in common physiological fluids such as 0.9% saline, Water-For-Injection, 5% dextrose, or glucose. The compounds may be administered in an effective non-toxic single dose of between about 50 mg. and about 2,500 mg. Alternatively, the compounds may be administered in divided doses of 2–4 times a day or every 4 hours.

The nucleus compounds of the invention represented by formulae 1, 5, and 6 wherein R is hydrogen are intermediates useful in the preparation of the corresponding acylamino compounds as described hereinabove. Likewise, the esters of the compounds are intermediates.

The following Examples are provided to further describe the present invention. In the Examples which follow, melting points were uncorrected. The abbreviations used are as follows: IR is infrared spectrum; UV is ultraviolet spectrum; NMR is nuclear magnetic resonance spectrum and, in the NMR spectra, the terms designating the type of signal are s=singlet, m=multiplet, d=doublet, br=broad, J=coupling constant, Hz=hertz, and pNB=p-nitrobenzyl; and FDMS is field desorption mass spectrum.

EXAMPLE 1

Allyl 7β-(2-thienylacetamido)-3-azido-3-cephem-4-carboxylate

To a solution of 0.409 g. of allyl 7β-(2-thienylacetamido)-3-chloro-3-cephem-4-carboxylate in 20 ml. of dimethylformamide cooled to about 5° C. in an ice bath were added 0.073 g. (1.1 eq.) of sodium azide. The reaction mixture was stirred in the cold for 1.5 hr. and then was transferred to a separatory funnel with cold ethyl acetate. The mixture was washed five times with water, once with brine, dried over sodium sulfate and evaporated to dryness in vacuo at 30° C. There were obtained 0.389 g. (94%) of the 3-azido compound.

IR (chloroform): 2100 and 1780 cm$^{-1}$

NMR (T-60, CDCl$_3$): δ3.58 (s, 2H, C$_2$—H), 3.83 (s, 2H, side chain CH$_2$), 4.72 (m, 2H, allyl CH$_2$), 4.93 (d J=4 Hz, 1H, C$_6$—H), 5.2–5.6 (m, 3H, allyl), 5.75 (d, d J=4, 8 Hz, 1H, C$_7$—H), and 7.50 (d, 1H, NH).

EXAMPLE 2 p-Nitrobenzyl 7β-(2-thienylacetamido)-3-azido-3-cephem-4-carboxylate

To a solution of 0.554 g. of p-nitrobenzyl 7β-(2-thienylacetamido)-3-methylsulfonyloxy-3-cephem-4-carboxylate in 10 ml. of DMF was added one molar equivalent (0.065 g.) of sodium azide and the mixture stirred at room temperature for 30 minutes. The mixture was transferred to a separatory funnel with ethyl acetate and the solution was washed three times with water, once with brine, dried over sodium sulfate and evaporated to dryness. The product, 0.523 g, obtained as a yellow froth showed a single spot on silica gel thin layer chromatography using 1:1, ethyl acetate:toluene for development and iodine for visualization.

EXAMPLE 3

Methyl 7β-(2-thienylacetamido)-3-azido-3-cephem-4-carboxylate

A twenty gram mixture of methyl 7β-(2-thienylacetamido)-3-chloro-3-cephem-4-carboxylate and the corresponding 2-cephem isomer was dissolved in 100 ml. of DMF, the solution cooled to about 5° C. in an ice bath, and 1.1 eg. (3.84 g.) of sodium azide were added. The reaction mixture was stirred at 5° C. for 30 minutes and for one hour without cooling. The reaction mixture was transferred to a separatory funnel with ethyl acetate and washed five times with water, once with brine, dried and evaporated to dryness to yield 19.5 g. of crude product as a brown solid.

IR (CHCl$_3$): 2100 cm$^{-1}$ (azide), 1770 cm$^{-1}$ (β-lactam carbonyl).

U.V. λmax 296 nm ε=8,000 (ethanol).

NMR (T60, CDCl$_3$): δ3.57 (br. s, 2H, C$_2$—H), 3.87 (s, 2H, side chain methylene), 4.97 (d, J=4 Hz, 1H, C$_6$—H), 5.70 (d, d J=4, 8 Hz, 1H, C$_7$—H).

EXAMPLE 4

Diphenylmethyl 7β-phenoxyacetamido-3-azido-3-cephem-4-carboxylate

To a solution of 1.728 g. of diphenylmethyl 7β-phenoxyacetamido-3-chloro-3-cephem-4-carboxylate in 25 ml. of DMF were added 1.05 eg. (0.220 g.) of sodium azide and the mixture was stirred at room temperature for one hour. The reaction mixture was transferred to a separatory funnel with ethyl acetate and washed three times with water, once with brine, dried, and evaporated to dryness. The crude product was purified by chromatography over 15 g. of silica gel using 500 ml. of toluene vs. 500 l. of 1:1 ethylacetate:toluene for elution. Multiple fractions were collected with fractions 24 to 31 being combined. The pooled fractions were evaporated to dryness to yield 0.795 g. of product as a yellow froth.

IR (CHCl$_3$) 2105 cm$^{-1}$, 1785 cm$^{-1}$.

NMR (CDCl$_3$) δ2.80, 3.27 (ABq J=16 Hz, 2H, C$_2$—H), 4.57 (s, 2H, side chain CH$_2$), 4.92 (d, J=4 Hz, 1H, C$_6$—H), 5.60 (d, d J=4, 8 Hz, 1H, C$_7$—H).

EXAMPLE 5

2,2,2-Trichloroethyl 7β-(2-thienylacetamido)-3-azido-3-cephem-4-carboxylate

To a solution of 2.926 g. of 2,2,2-trichloroethyl 7β-(2-thienylacetamido)-3-chloro-3-cephem-4-carboxylate in 17 ml. of DMF was cooled to 5° C. in an ice bath and 0.427 g. of sodium azide were added. The reaction mixture was stirred in an ice bath for 2 hr. and was then transferred to a separatory funnel with ethyl acetate. The mixture was washed with water and brine, dried and evaporated to dryness. There were obtained 2.54 g. of the crude 3-azido product.

IR (CHCl$_3$) 2110, 1788 cm$^{-1}$

UV λmax 300 nm ε=3,800 (ethanol).

NMR (T-60, CDCl$_3$): δ3.58 (s, 2H, C$_2$—H), 3.85 (s, 2H, side chain CH$_2$), 4.75, 4.98 (ABq J=11 Hz, 2H, ester), 5.00 (d, J=4 Hz, 1H, C$_6$—H), 5.73 (d, d J=4, 8 Hz, 1H, C$_7$—H).

EXAMPLE 6

Methyl 7β-acetamido-3-azido-3-cephem-4-carboxylate

A solution of 0.784 g. of methyl 7β-acetamido-3-chloro-3-cephem-4-carboxylate in 40 ml. of DMF was cooled to 5° C. in an ice bath and 0.193 g. of sodium azide were added. The reaction mixture was stirred in the cold for 45 minutes and then transferred to a separatory funnel with ethyl acetate. The mixture was washed with cold water, with brine, and was dried and evaporated to dryness. There were obtained 0.581 g. of the 3-azido ester product as a yellow solid.

IR (CHCl$_3$) 2105 cm$^{-1}$ (azide), 1770 cm$^{-1}$ (β-lactam carbonyl).

NMR (CDCl$_3$, T-60): δ2.07 (s, 3H, side chain CH$_3$), 3.58 (s, 3H, ester CH$_3$), 3.83 (s, 2H, C$_2$—H), 5.00 (d, J=4 Hz, 1H, C$_6$—H), 5.75 (d, d, J=4, 8 Hz, 1H, C$_7$—H).

EXAMPLE 7

7β-(2-Thienylacetamido)-3-azido-3-cephem-4-carboxylic acid

A solution of 0.625 g. of p-nitrobenzyl 7β-(2-thienylacetamido)-3-azido-3-cephem-4-carboxylate in 24 ml. of THF was diluted with 10 ml. of cold water and cooled in an ice-water bath. To the cold solution were added portionwise over about two hours 1.58 g. of zinc dust and sufficient 0.1N to 1N hydrochloric acid to maintain the pH of the mixture at about 4.3. Throughout the addition of zinc and acid the temperature of the reaction mixture was maintained at about 5° C. After the zinc dust addition was completed, the pH was adjusted to 2.7 with 1N hydrochloric acid and the mixture filtered. The filtrate was mixed with ethyl acetate and extracted twice with aqueous sodium bicarbonate. The aqueous layer was separated, layered with ethyl acetate, acidified with cold 1N hydrochloric acid, the organic layer separated, washed with brine, dried, and evaporated to yield 0.116 g. of the title acid as a pale yellow solid. The product was triturated with diethyl ether, filtered, and air dried to provide 80 mg. of the product acid as a yellow solid.

EXAMPLE 8 p-Nitrobenzyl 7β-(2-thienylacetamido)-2-phenylthio-3-amino-3-cephem-4-carboxylate To a solution of 0.675 g. of p-nitrobenzyl 7β-(2-thienylacetamido)-3-azido-3-cephem-4-carboxylate in 33 ml. of 1,2-dichloroethane were added 5 equivalents (0.74 g.) of thiophenol and the solution was heated at the reflux temperature for 90 min. The reaction mixture was evaporated to dryness and the reaction product residue was chromatographed over 8 g. of silica (Merck, toluene) using 500 ml. of toluene vs. 500 ml. of 50% ethyl acetate:toluene. The early fractions (23-26) contained a mixture of starting material and the title compound. The middle fractions (31-36) contained 0.035 g. of the title compound while the later fractions (45-59) contained 0.236 g. of the 3-amino ester.

p-Nitrobenzyl 7β-(2-thienylacetamido)-2-phenylthio-3-amino-3-cephem-4-carboxylate IR (CHCl$_3$) 1775 cm$^{-1}$, (β-lactam carbonyl)
MS (Field desorption): 582

NMR (T-60, CDCl₃): δ3.8 (s, 2H, thiophene H), 5.4 (m, 4H, C₆H, C₇H, and pNB), 6.4 (broad NH₂ protons).

p-Nitrobenzyl 7β-(2-thienylacetamido)-3-amino-3-cephem-4-carboxylate

Mp=211° C.—213° C. (methylene chloride, acetone, hexanes).

MS 475

IR (KBr) 1762 cm⁻¹ (β-lactam carbonyl)

UV (ethanol λmax=236 nm ε=14,500 (thiophene) λmax=286 nm ε=19,000 (pNB+conjugated NH₂).

NMR (DMSOd₆): δ3.08, 3,42 (AB, J=11 Hz, 2H, C₂H), 3.76 (s, 2H, side chain CH₂), 5.20 (m, 4H, C₆H, C₇H, and pNB), 7.6 (br. s., NH₂).

Elemental Analysis: Calculated: C, 50.62; H, 3.82; N, 11.81; O, 20.23; Found: C, 50.86; H, 3.70; N, 11.91; O, 20.09.

EXAMPLE 9

[2R-(2α,7α,8β)-4-Methoxy-9-oxo-8-[(2-thienylacetyl)-amino]-6-thia-1,3-diazabicyclo[5.2.0]non-3-ene-2-carboxylic acid, 2-propenyl ester To a solution of 4.06 g. of allyl 7β-(2-thienylacetamido)-3-azido-3-cephem-4-carboxylate in 75 ml. of acetone were added 75 ml. of methyl alcohol and the solution heated at the reflux temperature for one hour. The reaction mixture was evaporated to dryness and the residue chromatographed over silica gel using 600 ml. of toluene vs. 600 ml. of 80% ethyl acetate-toluene. Fractions containing the title compound were combined and evaporated to yield 1.31 g. of the title compound. The product was further purified by re-chromatography over silica gel using 500 ml. of toluene vs. 85% ethyl acetate-toluene.

Field Desorption M.S.=409

IR (CHCl₃) 1778 cm⁻¹, (β-lactam carbonyl).

Melting point: 125°-127° C. (from methylene chloride-hexane).

UV λmax=232 ε=9,700

NMR (T-60, CDCl₃): δ3.27, 3.52 (AB, J=16 Hz, 2H, —S—CH₂—), 3.63 (s, 3H, OCH₃), 3.83 (s, 3H, thiophene), 4.72 (m, 2H, allyl methylene), 5.2–5.5 (m, 5H, H₇ and H₈, and allyl), 6.00 (s, 1H, C₅H).

Elemental Analysis for C₁₇H₁₉N₃O₅S₂: Calculated: C, 49.86; H, 4.68; N, 10.26; Found: C, 49.63; H, 4.42; N, 9.97.

EXAMPLE 10

Reaction of p-nitrobenzyl 7β-(2-thienylacetamido)-3-azido-3-cephem-4-carboxylate with methanol To a solution of 4.95 g. of the 3-azido ester in 100 ml. of acetone were added 100 ml. of methyl alcohol and the solution was heated at the reflux temperature for one hour. The reaction mixture was evaporated to dryness and the residue was chromatographed over 14 g. of silica gel (Merck, toluene) using 800 ml. of 1:1 ethyl acetate:toluene, v:v vs. 800 ml. of toluene. The isomeric ring expanded products were eluted first followed by the 2-methoxy-3-amino-3-cephem ester.

The structures and physical data for the isolated products are as follows:

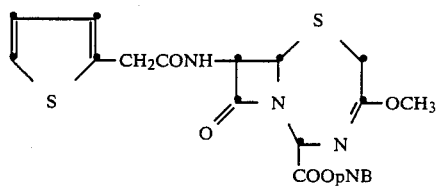

FDMS 504

IR (CHCl₃) 1773 cm⁻¹, (β-lactam carbonyl)

UV (C₂H₅OH): λmax 237 nm, ε=12,250 (thienyl) λmax 268 nm, ε=10,200 (pNB)

NMR (CDCl₃): δ3.10, 3.50 (AB, J=14 Hz, 2H, C₂H), 3.65 (s, 3H, OCH₃), 3.83 (s, 2H side chain CH₂), 5.38 (m, 4H, C₇H, C₈H, pNB), 6.05 (s, 1H, C₅H).

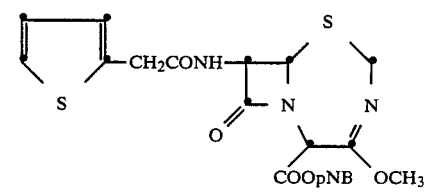

FDMS 504

IR (CHCl₃) 1775 cm⁻¹, (β-lactam carbonyl)

UV (C₂H₅OH): λmax 235 nm, ε=13,500 λmax 277 nm, ε=13,000

NMR (CDCl₃): δ3.63, (s, 3H, OCH₃), 3.83 (s, 2H side chain CH₂), 4.33, 4.55 (AB, J=14 Hz, 2H, C₂H), 5.1–5.6 (m, 5H, C₇H, C₈H, pNB).

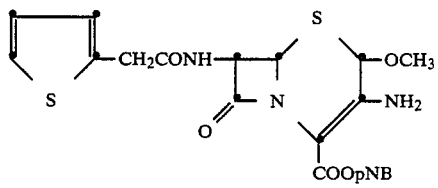

FDMS 504 m.p. 236° C. (from CH₂Cl₂-hexanes, white crystals)

IR (KBr) 1778 cm⁻¹

UV (C₂H₅OH) λmax 235 nm, ε=14,800 291-3 nm, ε=17,000

NMR (DMSOd₆): δ3.33, (s, 3H, OCH₃), 3.92 (s, 2H side chain CH₂), 5.1 (s, 1H, C₂H), 5.14–5.3 (m, 4H, C₆H, C₇H, and pNB).

Elemental Analysis: Calculated: C, 49.99; H, 4.00; N, 11.10, Found: C, 50.19; H, 4.01; N, 10.86.

EXAMPLE 11

[2R-(2α,7α,8β)],-4-Methoxy-9-oxo-8-[(2-thienylacetyl)-amino]-6-thia-1,3-diazabicyclo[5.2.0]non-3-ene-2-carboxylic acid sodium salt The [2R-(2α,7α,8β),],-4-methoxy-9-oxo-8-[(2-thienylacetyl)amino]-6-thia-1,3-diazabicyclo[5.2.0]non-3-ene-2-carboxylic acid 4-nitrobenzyl ester obtained as described by Example 10 was dissolved in 25 ml. of ethyl acetate and 0.121 g. of sodium bicarbonate and 25 ml. of water were first added to the solution followed by 0.362 g. of 5% Pd/C catalyst. The solution was hydrogenated under 50 psi hydrogen pressure in a Parr hydrogenation apparatus for 1 hr. at room temperature. The catalyst was filtered with the aid of a filter aid and the aqueous phase of the filtrate was separated and lyophilized. The product was obtained as a pale yellow solid in 4% yield.

IR (KBr) 1756 cm$^{-1}$, ($\beta$-lactam carbonyl)

NMR (D$_2$O): $\delta$3.45, (d, C$_5$H$_2$), 3.70 (s, OCH$_3$), 3.93 (s, side chain methylene), 5.1–5.7 (m, 2H $\beta$-lactam H), 5.83 (s, 1H, 2H).

EXAMPLE 12

[2R-(2$\alpha$,7$\alpha$,8$\beta$)],-3-Methoxy-9-oxo-8-[(2-thienylacetyl)-amino]-6-thia-1,4-diaza[5.2.0]non-3-ene-2-carboxylic acid sodium salt The 3-methoxy 1,4-diazo non-3-ene p-nitrobenzyl ester (0.276 g.) obtained as described by Example 10 was hydrogenated by following the procedure described by Example 10. There were obtained 0.129 g. (37%) of the title compound as a cream colored solid.

IR (KBr) 1760 cm$^{-1}$.

EXAMPLE 13

Sodium 7$\beta$-[(2-thienylacetyl)amino]-2-methoxy-3-amino-3-cephem-4-carboxylate The p-nitrobenzyl 7$\beta$-[(2-thienylacetyl)amino]-2-methoxy-3-amino-3-cephem-4-carboxylate, 0.399 g. obtained as described by Example 10 was hydrogenated over 5% Pd/C by following the procedure of Example 11. There were obtained 80 mg. (16%) yield of the title compound as a pale yellow solid.

IR (KBr) 1761 cm$^{-1}$.

EXAMPLE 14

[2R-(2$\alpha$,7$\alpha$,8$\beta$)],-4-Ethoxy-9-oxo-8-[(2-thienylacetyl)-amino]-6-thia-1,3-diazabicyclo[5.2.0]non-3-ene-2-carboxylic acid 4-nitrobenzyl ester A solution of 2.53 g of p-nitrobenzyl 7$\beta$-[(2-thienylacetyl)amino]-3-azido-3-cephem-4-carboxylate in 50 ml. of acetone and 50 ml. of ethyl alcohol was heated at the reflux temperature for 1.25 hr. and thereafter the solution was evaporated to dryness. The crude product showed three spots on a thin layer chromatogram. The predominant 4-ethoxy-1,3-diaza isomer (title compound) was separated from the other isomer by chromatography over 15 g. of silica gel using 600 ml. of toluene vs 600 ml. of 75% ethyl acetate-toluene. The title compound was obtained crystalline as fine white needles (0.713 g.) melting at about 154° C. to about 155° C. after recrystallization from methylethyl ketone-hexane.

The structure of the product was confirmed by X-ray analysis of the crystalline product.

IR (CHCl$_3$) 1775 cm$^{-1}$

NMR (T60, CDCl$_3$-DMSOd$_6$): $\delta$1.23 (t, 3H, ethoxy), 3.33 (s, 2H, C$_5$H), 3.80 (s, 2H, side chain methylene H), 4.1 (m, 2H), 5.42 (s, 4H, pNB ester +C$_7$H and C$_8$H), 6.13 (s, 1H, C$_2$H).

FDMS: 518

Elemental analysis: Theory: C, 50.96; H, 4.28; N, 10.80; Found: C, 50.98; H, 4.49; N, 10.57.

The predominant isomer (title compound) described above was eluted from the chromatography column in the early fractions. Later fractions contained all three isomers while the last fractions contained the isomeric product p-nitrobenzyl 7$\beta$-[(2-thienylacetyl)amino]-2-ethoxy-3-amino-3-cephem-4-carboxylate in a 4% yield.

NMR (CDCl$_3$—DMSOd$_6$, T-60) $\delta$1.07 (d, J=8 Hz, ethoxy CH$_3$), 3.87 (s, 2H, side chain methylene H), 3.80 (m, 2H, ethoxy methylene), 5.12 (s, 1H, C$_7$H), 5.2–5.5 (m, pNB ester, +C$_6$H and C$_7$H).

FDMS: 518

EXAMPLE 15

[2R-(2$\alpha$,7$\alpha$,8$\beta$)]-Oxo-4-phenoxy-8-[(2-thienylacetyl)-amino]-6-thia-1,3-diazabicyclo[5.2.0]non-3-ene-2-carboxylic acid, 4-nitrobenzyl ester.

A solution of 3.38 g. of p-nitrobenzyl 7$\beta$-[(2-thienylacetyl)amino]-3-azido-3-cephem-4-carboxylate in 90 ml. of acetone containing 3.175 g. of phenol was heated at the reflux temperature for one hour and was then evaporated to dryness.

The residue was chromatographed over 18 g. of silica gel (toluene) using 600 ml. of toluene vs. 600 ml. of 75% ethyl acetate-toluene. The product (title compound) crystallized in the eluate of fractions 41–43 and 49–50 and was filtered to provide 0.175 g. From the filtrate were obtained 0.338 g. of additional product. The first crop (0.175 g.) was recrystallized from methylene chloride to give fine white needles melting at about 165° C. to about 167° C.

Elemental analysis: Theory: C, 55.11; H, 3.91; N, 9.89
Found: C, 54.84; H, 3.66; N, 9.66

FDMS: 566

IR (KBr): 1779 cm$^{-1}$

UV (C$_2$H$_5$OH): $\lambda$max 235 nm, $\epsilon$=10,000, $\lambda$max 265 nm, $\epsilon$=7,500

EXAMPLE 16

[2R-(2$\alpha$,7$\alpha$,8$\beta$)]-4-Methoxy-9-oxo-8-[$\alpha$-(2-aminothiazol-4-yl)-$\alpha$-methoxyiminoacetyl)amino]-6-thia-1,3-diazabicyclo[5.2.0]non-3-ene-2-carboxylic acid The title compound is obtained by acylating the nucleus, [2R-(2$\alpha$,7$\alpha$,8$\beta$)]-4-methoxy-9-oxo-8-amino-6-thia-1,3-diazabicyclo[5.2.0]non-3-ene-2-carboxylic acid, 4-nitrobenzyl ester (formula 6',

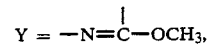

R$_1$=pNB), in methylene chloride with 2-(2-tritylaminothiazol-4-yl)-2-methoxyiminoacetic acid in the presence of an equimolar amount of dicyclohexylcarbodiimide. The aminoprotecting trityl group and the ester group are removed with formic acid and zinc-HCl reduction, respectively, to provide the title compound represented by the formula

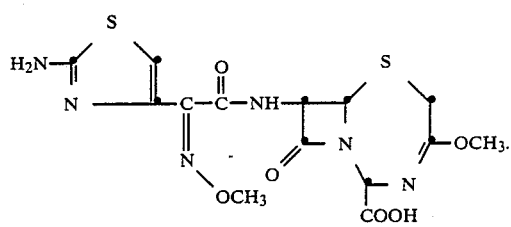

We claim:
1. The compound of the formula

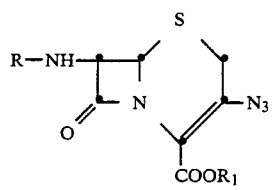

wherein
R is an acyl group of the formula

wherein
$R^1$ is $C_1$–$C_4$ alkyl, $C_1$–$C_4$ alkyl substituted by halogen or cyano;
or R is an aroyl or aralkanoyl group of the formula

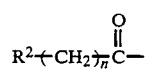

wherein
$R^2$ is phenyl or a mono substituted phenyl group of the formula

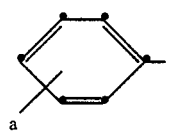

wherein
a is halogen, amino, hydroxy, $C_1$–$C_4$ alkyl, $C_1$–$C_4$ alkoxy, cyano, hydroxymethyl, aminomethyl, carboxamido, carboxymethyl, or $C_1$–$C_4$ alkoxycarbonylmethyl;
or $R^2$ is a di- or tri-substituted phenyl group of the formula

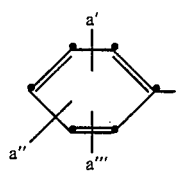

wherein
a', a'', and a''' are independently hydrogen, halogen, hydroxy, $C_1$–$C_4$ alkyl, or $C_1$–$C_4$ alkoxy; and
n is 0 or 1;
or R is a heteroarylalkanoyl group of the formula

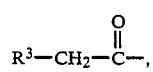

wherein
$R^3$ is

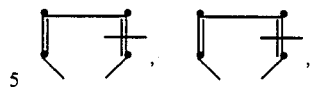

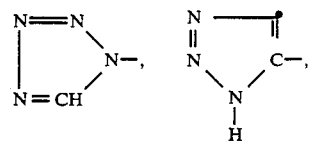

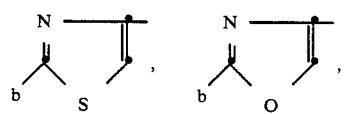

wherein
each b is amino, protected amino, $C_1$–$C_3$ alkyl or phenyl;
or R is an aryloxyacetyl or arylthioacetyl group of the formula

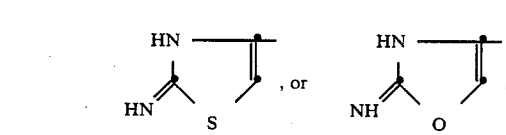

wherein
$R^2$ has the same meanings as defined above and Z is O or S;
or R is an α-substituted aralkanoyl or heteroarylalkanoyl substituted group of the formula

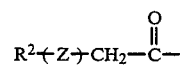

wherein
$R^4$ is $R^2$, as defined above, and in addition is thienyl, furyl, or 1,4-cyclohexadienyl; Q is hydroxy, formyloxy, carboxy, the sulfo group —$SO_3H$, or amino;
or R is an oximino-substituted aralkanoyl or heteroarylalkanoyl group of the formula

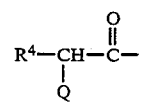

wherein
$R^5$ is $R^2$ and $R^3$ as each is defined above, and $R^6$ is hydrogen or $C_1$–$C_3$ alkyl;
$R_1$ is hydrogen or a carboxy protecting group;
and when $R_1$ is hydrogen the pharmaceutically acceptable non-toxic salts thereof.

2. The compound of claim 1 wherein R is an acyl group $R^1$—C(O)—.

3. The compound of claim 1 wherein R is an acyl group

4. The compound of claim 3 wherein $R^2$ is phenyl and n is 1.

5. The compound of claim 3, 7β-phenylacetylamino-3-azido-3-cephem-4-carboxylic acid and the pharmaceutically acceptable, non-toxic salts thereof.

6. The compound of claim 1 wherein R is an acyl group

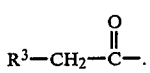

7. The compound of claim 6 wherein $R_3$ is thienyl, furyl, 2-aminothiazole, or tetrazole.

8. The compound of claim 7, 7β-(2-thienylacetylamino)-3-azido-3-cephem-4-carboxylic acid and the pharmaceutically acceptable non-toxic salts thereof.

9. The compound of claim 1 wherein R is an acyl group

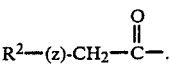

10. The compound of claim 9, 7β-phenoxyacetylamino-3-azido-3-cephem-4-carboxylic acid.

11. The compound of claim 1 wherein R is an acyl group

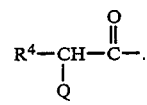

12. The compound of claim 1 wherein R is an acyl group

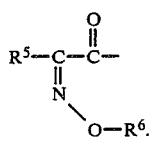

* * * * *